United States Patent
Alary et al.

(10) Patent No.: US 11,241,563 B2
(45) Date of Patent: Feb. 8, 2022

(54) MICRONEEDLE ARRAYS AND METHODS FOR MAKING AND USING

(71) Applicant: JOHNSON & JOHNSON CONSUMER INC., Skillman, NJ (US)

(72) Inventors: Marc Alary, Skillman, NJ (US); Peyton Hopson, Jacksonville, FL (US); Jan-Joo Liu, Skillman, NJ (US); Erik Lunde, Skillman, NJ (US); Bharat Patel, Skillman, NJ (US); Emanuel Morano, Totowa, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 35 days.

(21) Appl. No.: 15/848,905

(22) Filed: Dec. 20, 2017

(65) Prior Publication Data

US 2018/0177990 A1   Jun. 28, 2018

Related U.S. Application Data

(60) Provisional application No. 62/437,800, filed on Dec. 22, 2016.

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0053* (2013.01)

(58) Field of Classification Search
CPC ...... A61M 37/0015; A61M 2037/0023; A61M 2037/003; A61M 2037/0038; A61M 2037/0046; A61M 2037/0053; A61B 5/150977; A61B 5/150984
See application file for complete search history.

(56) References Cited

U.S. PATENT DOCUMENTS

| | | | |
|---|---|---|---|
| 6,611,707 B1 | 8/2003 | Prausnitz et al. | |
| 6,623,457 B1 * | 9/2003 | Rosenberg | A61B 17/205 604/191 |
| 7,030,411 B2 | 4/2006 | Krulevitch et al. | |
| 7,540,717 B2 | 6/2009 | Sheng et al. | |
| 8,343,425 B1 | 1/2013 | Li et al. | |
| 8,956,637 B2 | 2/2015 | Dubrow et al. | |

(Continued)

FOREIGN PATENT DOCUMENTS

| | | |
|---|---|---|
| CN | 105126243 A | 12/2015 |
| CN | 204890945 U | 12/2015 |

(Continued)

OTHER PUBLICATIONS

U.S. Appl. No. 16/457,031, filed Jun. 28, 2019, US20200001064A1, Jan. 2, 2020, Pending, Alary et al.

(Continued)

*Primary Examiner* — Nilay J Shah

(57) ABSTRACT

An array of differing microneedles can be accurately achieved including a film having first and second, outwardly facing major surfaces. The first, outwardly facing major surface has a plurality of stratum corneum piercing microneedles extending therefrom, and the plurality of microneedles includes a plurality of first microneedles having a first benefit agent and a plurality of second microneedles having a second benefit agent.

8 Claims, 4 Drawing Sheets

(56) References Cited

U.S. PATENT DOCUMENTS

| | | | |
|---|---|---|---|
| 9,060,842 B2 | 6/2015 | Karp et al. | |
| 2003/0083645 A1 | 5/2003 | Angel et al. | |
| 2004/0121528 A1 | 6/2004 | Krulevitch et al. | |
| 2004/0267205 A1 | 12/2004 | Stemme et al. | |
| 2007/0078414 A1* | 4/2007 | McAllister | A61B 17/205 604/272 |
| 2008/0183144 A1* | 7/2008 | Trautman | A61M 37/0015 604/272 |
| 2009/0182306 A1* | 7/2009 | Lee | A61K 9/0021 604/506 |
| 2010/0221314 A1* | 9/2010 | Matsudo | A61M 37/0015 424/449 |
| 2010/0228203 A1 | 9/2010 | Quan et al. | |
| 2011/0028905 A1* | 2/2011 | Takada | A61K 9/0021 604/180 |
| 2011/0087195 A1 | 4/2011 | Uhland et al. | |
| 2011/0244010 A1 | 10/2011 | Doshi | |
| 2012/0052234 A1 | 3/2012 | Natarajan et al. | |
| 2012/0220980 A1 | 8/2012 | Ross | |
| 2012/0265145 A1* | 10/2012 | Mefti | A61M 37/0015 604/173 |
| 2013/0116523 A1 | 5/2013 | Jung et al. | |
| 2014/0005606 A1 | 1/2014 | Chen et al. | |
| 2014/0081295 A1 | 3/2014 | Lau et al. | |
| 2014/0363610 A1 | 12/2014 | Sameoto | |
| 2015/0030642 A1 | 1/2015 | Wu et al. | |
| 2015/0141895 A1 | 5/2015 | Tuma | |
| 2015/0144259 A1 | 5/2015 | Laulicht et al. | |
| 2015/0329743 A1 | 11/2015 | Lu et al. | |
| 2016/0051195 A1 | 2/2016 | Pang et al. | |
| 2016/0346466 A1 | 12/2016 | Wang et al. | |
| 2017/0341075 A1 | 11/2017 | Sirkis et al. | |
| 2018/0311486 A1 | 11/2018 | Park | |
| 2020/0001064 A1 | 1/2020 | Alary et al. | |
| 2020/0001065 A1 | 1/2020 | Alary et al. | |

FOREIGN PATENT DOCUMENTS

| | | | |
|---|---|---|---|
| EP | 1699403 A | 9/2006 | |
| EP | 2125608 A | 12/2009 | |
| EP | 2548608 A | 1/2013 | |
| JP | 2007089792 A | 4/2007 | |
| JP | 2010069242 A | 4/2010 | |
| JP | 2010069253 A | 4/2010 | |
| JP | 2010233673 A | 10/2010 | |
| JP | 2016171888 A | 9/2013 | |
| JP | 2015226649 A | 12/2015 | |
| KR | 20160121370 A | 10/2016 | |
| WO | 2005/103303 A | 11/2005 | |
| WO | 2009/081122 A | 7/2009 | |
| WO | 2010/022252 A | 2/2010 | |
| WO | 2013/131215 A | 9/2013 | |
| WO | WO-2014142135 A1 * | 9/2014 | A61M 37/0015 |
| WO | 2015/167991 A | 11/2015 | |
| WO | 2016/052818 A | 4/2016 | |

OTHER PUBLICATIONS

U.S. Appl. No. 16/457,125, filed Jun. 28, 2019, US20200001065A1, Jan. 2, 2020, Pending, Alary et al.

U.S. Appl. No. 62/691,699, filed Jun. 29, 2018, Expired, Alary et al.

International search report dated Jun. 8, 2018, for international application PCT/US2017/067790.

\* cited by examiner

MICRONEEDLE ARRAYS AND METHODS FOR MAKING AND USING

CROSS-REFERENCE TO RELATED APPLICATIONS

This application claims the benefit of U.S. provisional application 62/437,800 filed on Dec. 22, 2016.

FIELD OF THE INVENTION

The present invention relates to devices for the transdermal administration of benefit agents to patients through the skin. More particularly, this invention relates to microneedle arrays comprising a plurality of benefit agents, and methods for making and using these arrays.

BACKGROUND OF THE INVENTION

Transdermal drug delivery provides several advantages over other routes for administering a benefit agent formulation to a patient. For example, oral administration of some benefit agents may be ineffective because the benefit agent is destroyed in the gastrointestinal tract or eliminated by the liver, both of which are avoided by transdermal drug delivery. Parenteral injection with a conventional hypodermic needle also has drawbacks, as it is often painful and inconvenient.

Transdermal drug delivery avoids these problems. However, there are obstacles to its use. In particular, the physical barrier properties of the stratum corneum of human skin pose a significant challenge to transdermal drug delivery. These barrier properties only allow relatively small molecules to be transported through the intact stratum corneum, and many useful drugs are too large to pass through the stratum corneum without some type of modification of the stratum corneum or other transport enhancement. Various transdermal enhancement methods are known, including those based on iontophoresis, ultrasound, and chemical penetration enhancers. However, these methods may be inadequate to assist in the delivery of many medications through an intact skin layer and/or they may be inconvenient or undesirably complicated to use.

To address the challenge of intact skin, a variety of microneedle-array based drug delivery devices have been developed. These known microneedle array generally fall into one of two design categories: (1) solid microneedles arrays with no active component, and (2) microneedles with a central hollow bore, which are similar to conventional hypodermic needle.

Solid microneedle arrays can pre-condition the skin by piercing the stratum corneum and the upper layer of epidermis to enhance percutaneous drug penetration prior to topical application of a biologic-carrier or a traditional patch. If solid microneedle arrays are kept in the skin, then the drug cannot readily flow into and through the holes in the skin because the holes remain plugged by the microneedles. This method has been shown to significantly increase the skin's permeability; however, this method provides only limited ability to control the dosage and quantity of delivered drugs or vaccine.

To increase the dosage control some methods uses solid microneedles that are surface-coated with a drug. Although this method provides somewhat better dosage control, it greatly limits the quantity of drug delivered. Also, the deposition process is unreliable, and the thin layer of drug formulation on the microneedle could be easily chipped off of the microneedle during storage, transport, or administration (insertion) of the microneedles. The application of a thicker and stronger layer of drug formulation can be undesirable because it reduced the sharpness of the microneedles and therefore made insertion more difficult and painful. This shortcoming has limited the widespread application of this approach and precludes, for example, the simultaneous delivery of optimal quantities of combinations of antigens and/or adjuvant in vaccine applications.

Microneedles with a central hollow bore attached to a reservoir of benefit agents are also known. The syringe needle-type characteristics of these arrays can significantly increase the speed and precision of delivery, as well as the quantity of the delivered agent. However, reservoir-based microneedle arrays are expensive to make and require complex and expensive micromachining procedures. In particular, it is difficult to make sharp tips on hollow microneedles with machining techniques. Consequently, insertion of the microneedles into a patient's skin can be difficult and often painful. In addition, the central bore of the microneedle is quite small and may be easily plugged by skin tissue during the insertion process, thereby blocking the drug delivery conduit. It may be even slower than the diffusion of the drug through the stratum corneum in the absence of the microneedle. It therefore would be desirable to provide a microneedle array for drug delivery that avoids the disadvantages associated with known hollow microneedle array designs.

Also known methods involve using solid microneedle arrays that are biodegradable, bioabsorbable, or dissolvable. This method combines the physical toughness of solid microneedles with relatively high bioactive material capacity, while retaining desired attributes of simple fabrication, storage and application. Current fabrication approaches for dissolvable polymer-based microneedles generally use microcasting processes. For example, a primary master mold is commonly produced using a combination of complex lithographic and laser etching technologies. However, lithographic and laser-based technologies are limited in the range of geometric features they can create, and the materials to which they can be applied. Also, these highly complex fabrication technologies do not allow rapid or low cost fabrication of master molds, which can be particularly useful for systematic testing of the bio-effectiveness of various different microneedle and array geometries.

Finally, the microcasting process for producing dissolvable polymer-based microneedle arrays is limited to producing arrays of a single composition. If there is a desire for personalized treatment requiring dissolvable arrays using microneedles with different compositions or benefit agents, the microcasting process cannot produce such arrays.

In summary, transdermal delivery of benefit agents using microneedle-array based devices offer attractive theoretical advantages over prevailing oral and needle-based drug delivery methods. However, considerable practical limitations exist in the design, fabrication, and testing associated with microneedle arrays constructed using conventional processes. Also, there is a need for a simple, effective, and economically desirable device for transdermal administration of using microneedle arrays simultaneously delivering more than one benefit agent.

SUMMARY OF THE INVENTION

Surprisingly, we have found that an array of differing microneedles can be accurately achieved including a film having first and second, outwardly facing major surfaces.

The first, outwardly facing major surface has a plurality of stratum corneum piercing microneedles extending therefrom, and the plurality of microneedles includes a plurality of first microneedles having a first benefit agent and a plurality of second microneedles having a second benefit agent.

DETAILED DESCRIPTION OF THE INVENTION

The present invention relates to devices for the transdermal administration of a plurality of benefit agents to patients through the skin using microneedle array systems, and methods for making and employing these systems. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

As used herein the specification and the claims, the term "topical" and variants thereof mean "of or applied to an isolated part of the body". This includes, without limitation skin, mucosa, and enamel, either directly or through an intermediate such as a biofilm.

As used herein, "benefit agent" means an ingredient or material that provides a benefit, e.g., improves, relieves, reduces, or treats symptoms or conditions of the skin or body, either cosmetic or therapeutic. Other terms of use for "benefit agent" include "biologic," "active component," or "bioactive material". These terms all refer to pharmaceutically active agents, such as analgesic agents, anesthetic agents, anti-asthmatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, vaccines, and the like. The benefit agent material can comprise dissoluble materials, insoluble but dispersible materials, natural or formulated macro, micro and nano particulates, and/or mixtures of two or more of dissoluble, dispersible insoluble materials and natural and/or formulated macro, micro and nano particulates.

In some embodiments, the microneedle array systems described herein are flexible so as to be conformable to the three-dimensional shape corresponding to the site of delivery of benefiting agent substance to the skin of the consumer. In other embodiments, the microneedle array may be more rigid; built as the described three-dimensional shape to match the topical contour. The array may have varying personalized area-specific treatment zones to enable the treatment application more effectively. With an array matched to the individual user's body part profile as physical guides, the application becomes easier and more effective, and can help in locating specific target zones to the precise area for applications.

Figure 1:
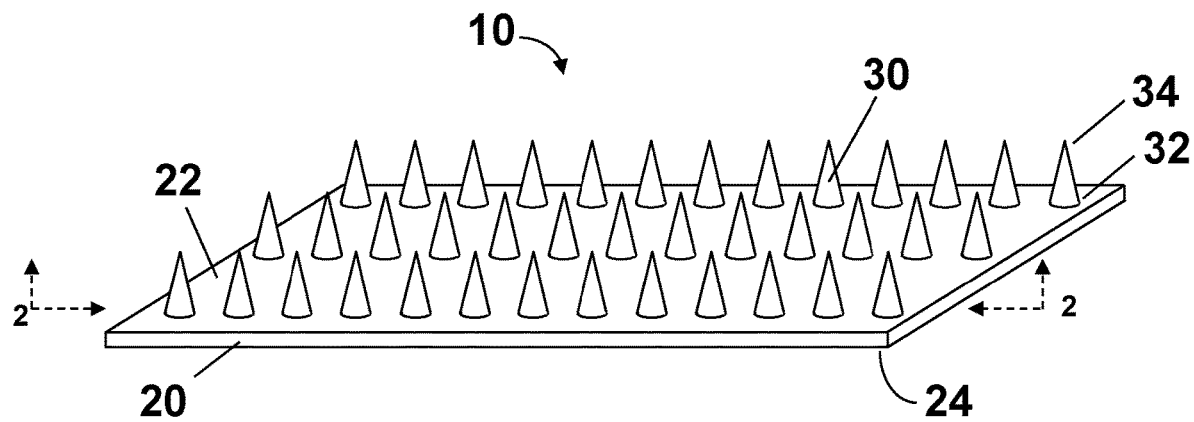
FIG. 1 is a perspective view of one embodiment of a microneedle array.

Referring to the drawings, FIG. 1 is a perspective view of one embodiment of a microneedle array 10 which may be used in the present invention. Microneedle array 10 includes a film 20 having first outwardly facing major surface 22 and second outwardly facing major surface 24. First outwardly facing major surface 22 has a plurality of stratum corneum piercing microneedles 30 extending therefrom. Each microneedle 30 has a proximal end 32 and a distal end 34, where proximal end 32 is the end of microneedle 30 disposed on first outwardly facing major surface 22 of a microneedle array 10.

In FIG. 1, microneedle array 10 is shown to have a rectangular footprint. Film 20 of microneedle array 10 may also have a variety of shapes, depending on the location of skin treatment. Possible shapes of the footprint left by film 20 include, but are not limited to, squares, rectangles, triangles, circles, ovals, kidneys, stars, crosses, characters, etc. The corners of such shapes, if any, may be angular or curved to reduce potential lift/removal points. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

Film 20 element of microneedle array 10 preferably is relatively thin and flexible, so that they preferably readily conform to the user's skin and are comfortable to wear, both because of the flexibility and conformability, as well as from the thinness. Microneedle array 10 of the present invention may be intended for extended wear preferably are also formed to be aesthetically elegant without either peeling, wrinkling, cracking, or appearing greasy or tacky, or otherwise unpleasant or unsightly in nature. Microneedle array 10 preferably is formed with sufficient rigidity and integrity to be able to withstand normal use when on the skin. In some embodiments, microneedle array 10 of the invention preferably is formed with sufficient strength to stay intact on the skin when exposed to normal external forces that the skin may experience, rubbing of clothing.

In some embodiments, first outwardly facing major surface 22 of film 20 has disposed thereon an adhesive layer. The adhesive layer may be used to give microneedle array 10 the sufficient strength to stay intact on the skin when exposed to normal external forces. Other means of creating sufficient strength to microneedle array 10 so that the array stays intact on the skin will be discussed below.

Figure 2:
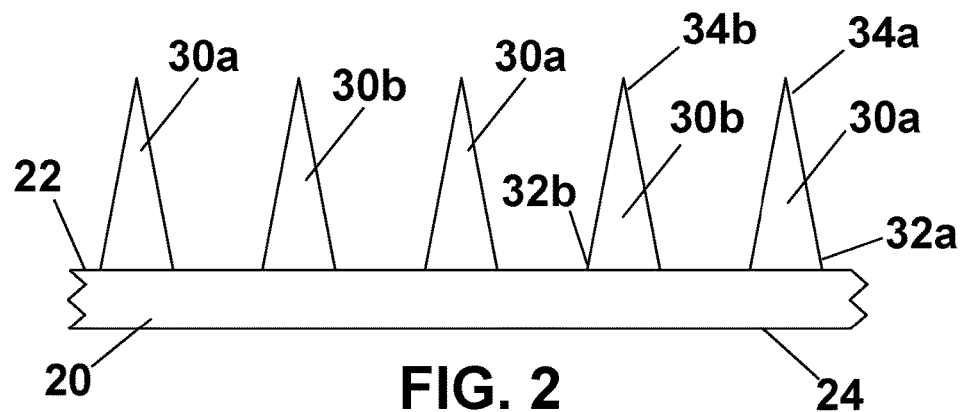
FIG. 2 is a cross-sectional view of a section of the microneedle array of FIG. 1 along the 2-2 plane.

FIG. 2 is a cross-sectional view of a section of the microneedle array along the 2-2 plane of FIG. 1. The figure shows a plurality of first stratum corneum piercing microneedles 30a and a plurality of second stratum corneum piercing microneedles 30a. Each microneedle 30a has a proximal end 32a and a distal end 34a, while each microneedle 30b has a proximal end 32b and a distal end 34b. Plurality of first microneedles 30a comprises a first benefit agent and plurality of second microneedles 30b comprises a second benefit agent.

The dimensions of stratum corneum piercing microneedles 30a, 30b may vary depending on a variety of factors such as the type of benefit agent to be delivered, the dosage of the benefit agent to be delivered, and the desired penetration depth. Generally, the stratum corneum piercing microneedles are constructed to provide skin-piercing and benefit agent delivery functions and thus will be designed to be sufficiently robust to withstand insertion into and withdrawal from the skin. Each microneedle has a length of about 1 micrometer (μm) to about 5000 micrometers (μm), or about 1 μm to about 500 μm, or about 100 μm to about 500 μm. The penetration length of the microneedles into the biological barrier is about 50 rpm to about 200 μm. In addition, each of the microneedles has a width of about 1 pun to about 500 μm. Furthermore, each microneedle has a thickness of about 1 μm to about 200 nm. It will be understood by one skilled in the art that the width and thickness of the stratum corneum piercing microneedle may vary along its length. For instance, the base portion may be wider (thicker) than the body portion, or the body portion may have a slight taper approaching the tip portion.

Figure 3:
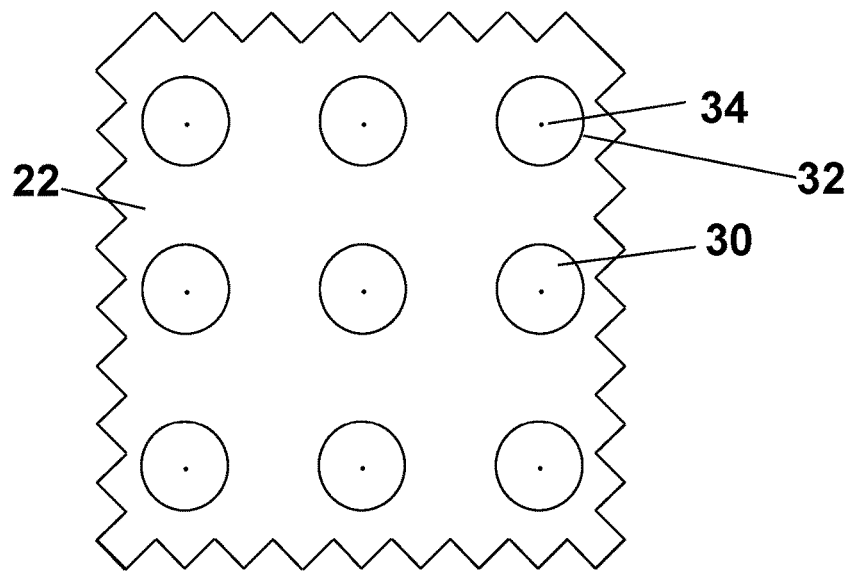
FIG. 3 is a top view of a section of the microneedle array of FIG. 1.

FIG. 3 is a top view of a section of the microneedle array of FIG. 1. The figure shows stratum corneum piercing microneedles 30 which extend from first outwardly facing major surface 22 of microneedle array 10. Each microneedle 30 has a proximal end 32 and a distal end 34. As shown in the figure, microneedles 30 are arranged in a square pattern on first outwardly facing major surface 22 of microneedle array 10. In other embodiments, microneedles 30 are arranged in other patterns, such as triangular, square, pentagonal, hexagonal, octagonal, etc.

Figure 4:
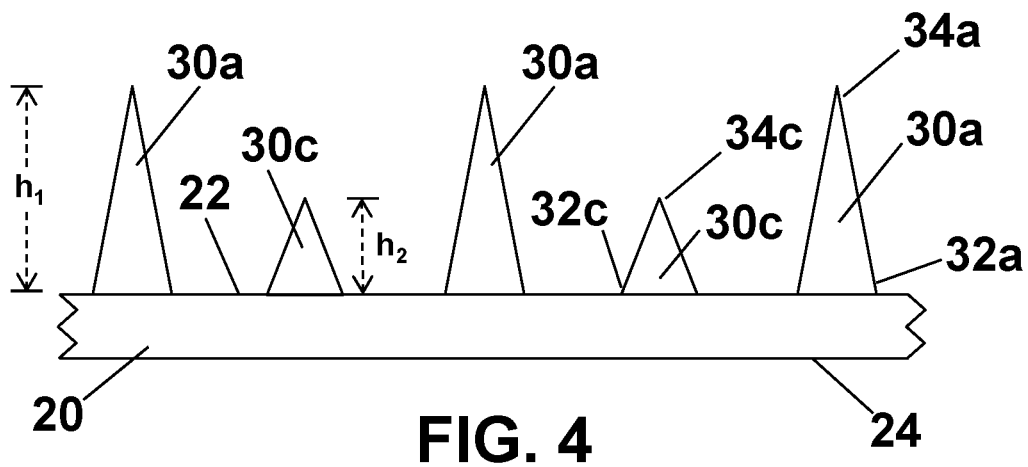
FIG. 4 is a cross-sectional view of a section of a second embodiment microneedle array.

Microneedles 30 in microneedle array 10 of the invention may also be of a variety of lengths and geometries. FIG. 4 is a cross-sectional view of a section of a second embodiment microneedle array. In this embodiment, plurality of first stratum corneum piercing microneedles 30a comprise a first benefit agent and plurality of second stratum corneum piercing microneedles 30c comprise a second benefit agent. In addition, plurality of first microneedles 30a extend from first outwardly facing major surface 22 of film 20 to a height of $h_1$, while plurality of second microneedles 30b extend from first surface 22 of film 20 to a height of $h_2$. In this embodiment, there may be a desire for a deeper penetration into the skin of the user for first benefit agent contained in plurality of first microneedles 30a than from second benefit agent contained in plurality of second microneedles 30b.

Although the figure shows first stratum corneum piercing microneedles 30a are of uniform height $h_1$, while second stratum corneum piercing microneedles 30b are of uniform height $h_2$, it is to be understood that in other embodiments the microneedles may be of any number of different heights. In addition, it is important to note that neither all microneedles 30a are comprised of a first benefit agent, nor that all microneedles 30b are comprised of a second benefit agent. In some embodiments, some of the microneedles will not comprise any benefit agent.

Generally, stratum corneum piercing microneedles 30 can be in any elongated shape suitable for providing the skin piercing and benefit agent delivery, with minimal pain to the patient. In various embodiments, an individual microneedle is substantially cylindrical, wedge-shaped, cone-shaped, or triangular (e.g., blade-like). The cross-sectional shape (cut along a plane approximately parallel to the planar substrate or approximately perpendicular to the longitudinal axis of the microneedle) of the microneedle, or at least the portion of the microneedle that is penetrable into the skin, may take a variety of forms, including rectangular, square, oval, circular, diamond, triangular, or star-shaped.

The tip portions of stratum corneum piercing microneedles 30 are designed to pierce a biological barrier, e.g., to pierce the stratum corneum of the skin of a patient, to deliver benefit agents into the patient's tissue. Preferably, the tip portion of each microneedle should be sufficiently small and sharp to enable piercing and penetration of the skin with minimal pain. In a preferred embodiment, individual microneedles 30 are tapered from the first, outwardly facing major surface 22 of microneedle array 10 to a point distal therefrom. In various embodiments, the tapered tip portion may be in the form of an oblique angle at the tip, or a pyramidal or conical or triangular shape.

Figure 5:
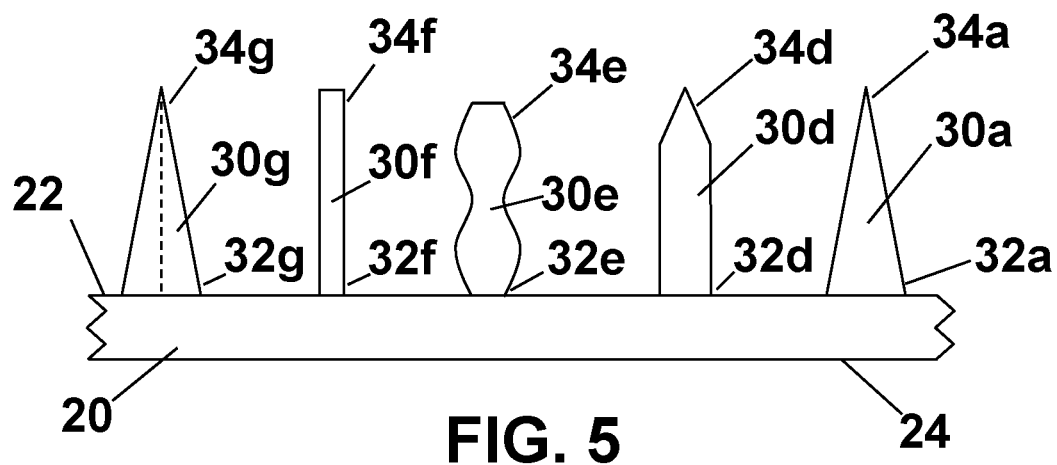
FIG. 5 is a cross-sectional view of a section of a third embodiment microneedle array.

FIG. 5 is a cross-sectional view of a section of a third embodiment microneedle array showing a variety of stratum corneum piercing microneedle shapes. Microneedle 30a is conical in shape, with a taper from proximal end 32a to distal end 34a. Microneedle 30d has a cylindrical proximal end 32d, which tapers to a point at distal end 34d. Microneedle 30e has a proximal end 32e and a distal end 34e, and has an undulating shape. Microneedle 30f is cylindrical in shape, with no taper from proximal end 32f to distal end 34f. Finally, microneedle 30g is pyramidal in shape, with a taper from proximal end 32g to distal end 34g.

Although FIG. 5 shows all stratum corneum piercing microneedles 30 of substantially uniform height, it is to be understood that in other embodiments the microneedles may be of any number of different heights. In addition, microneedles 30a, 30d, 30e, 30f, and 30g comprise at least one benefit agent. Some comprise a first benefit agent, while others comprise a second benefit agent, so that microneedle arrays 10 comprises microneedles with two distinct benefit agents. Of course, not all microneedles 30 of any given shape or height are required to all comprised either first or second benefit agent.

Figure 6:
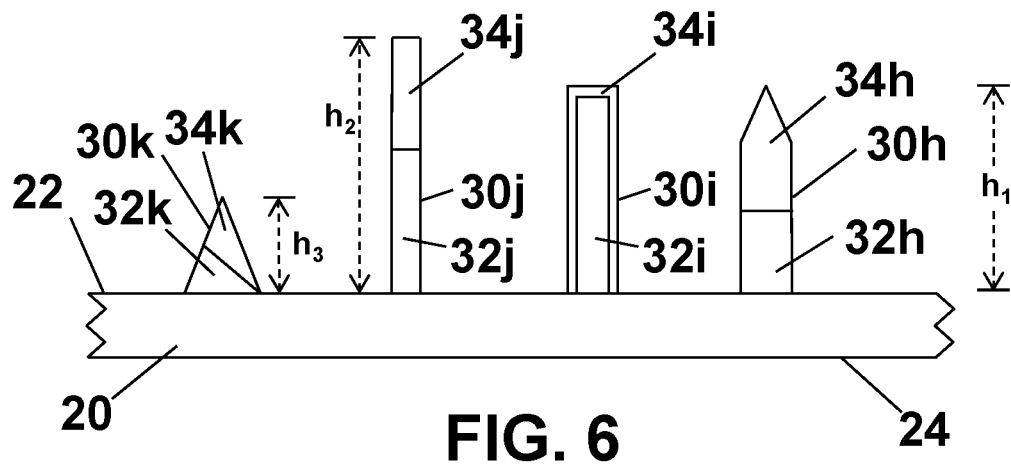
FIG. 6 is a cross-sectional view of a section of a fourth embodiment microneedle array.

Microneedle arrays 10 of the present invention may also comprise stratum corneum piercing microneedles 30 comprised of multiple compositions. FIG. 6 is a cross-sectional view of a section of a fourth embodiment microneedle array 10 with such microneedles. The figure shows four different microneedles, with the microneedles being of variable heights, and comprising at least two distinct benefit agents. Microneedle 30h has a cylindrical proximal end 32h, which tapers to a point at distal end 34h. In addition, proximal end 32h of microneedle 30h is of a different composition than distal end 34h of microneedle 30h. Microneedle 30i is cylindrical, and has a core section 32i and a sheath section 34i. Here, core section 32i is of a different composition than sheath section 34i. Microneedle 30j has a cylindrical proximal end 32j and a cylindrical distal end 34j, and has a substantially linear form. Here, proximal end 32j of microneedle 30j is of a different composition than distal end 34j of microneedle 30j. Finally, microneedle 30k is conical in shape, with a taper from proximal end 32k to distal end 34k Proximal end 32k of microneedle 30k is of a different composition than distal end 34k of microneedle 30k Special attention is now paid to microneedle 30i. Microneedle 30i comprises a core section 32i and a sheath section 34i. Core section 32i is of a different composition than sheath section 34i. In some embodiments, core section 32i does not have the mechanical strength or rigidity to penetrate the skin, while sheath section 34i does. In other embodiments, sheath section 34i does not have the mechanical strength or rigidity to penetrate the skin, while core section 32i does. Therefore, at least one of the sheath sections comprised a rigid composition. So, materials/active/drugs which are not strong enough to penetrate the skin can still be delivered.

Special attention is now paid to microneedle 30*j*. Microneedle 30*j* has a cylindrical distal end 34*j*, and has an initial, substantially linear form. Upon insertion into the skin, distal end 34*j* is designed to curve to form a hook-like structure or form. As mentioned earlier, in some embodiments, first outwardly facing major surface 22 of film 20 has disposed thereon an adhesive layer to give microneedle array 10 the sufficient strength to stay intact on the skin when exposed to normal external forces. In some embodiments, microneedle array 10 may have a plurality of microneedles which form hook-like structures. Hook-like microneedles 30*j*, once they penetrate the skin, may have sufficient strength so as to hold microneedle array 10 intact on the skin during use.

The figure also shows that the stratum corneum piercing microneedles are of different lengths. In this embodiment, microneedles 30*h* and 30*i* extend from first outwardly facing major surface 22 of film 20 to a height of $h_1$, microneedle 30*j* extends from first surface 22 of film 20 to a height of $h_2$, and microneedle 30*k* extends from first surface 22 of film 20 to a height of $h_3$. In this embodiment, there may be a desire for a deeper penetration into the skin of the user for the different benefit agents.

Although FIG. 6 figure shows stratum corneum piercing microneedles 30 of different heights, it is to be understood that in other embodiments the microneedles may all be of the same height, or any number of different heights. In addition, it is important to note that all microneedles 30 are neither comprised of a first benefit agent nor a second benefit agent. Also, not all microneedles 30 are composed of multiple benefit agents. In some embodiments, some of the stratum corneum piercing microneedles will not comprise any benefit agent.

Figure 7:
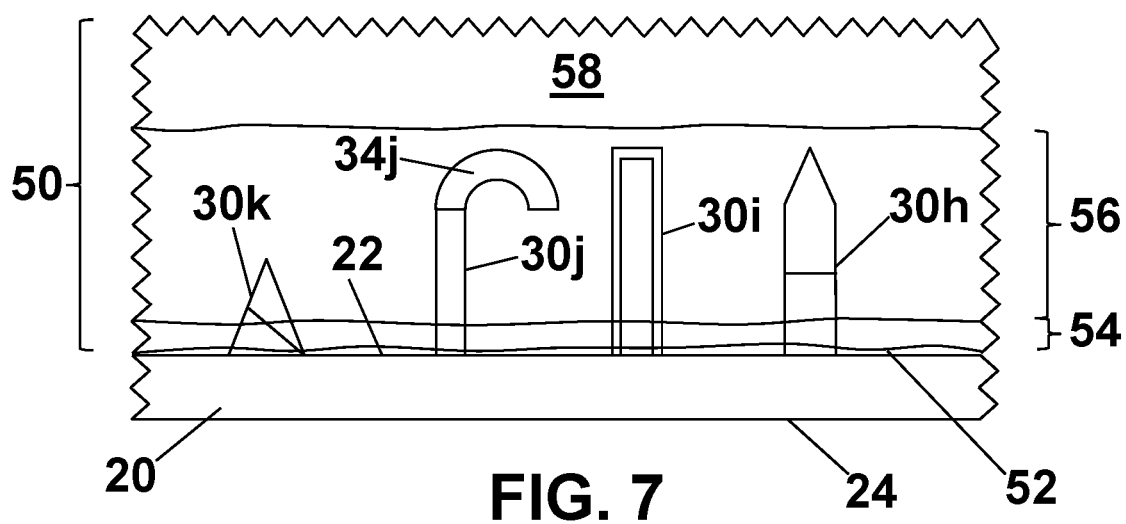
FIG. 7 is a cross-sectional view of a section of the microneedle array of FIG. 6 after the microneedles have penetrated the patient's skin.

The different sizes, compositions, and geometries of the stratum corneum piercing microneedles are demonstrated in a prophetic use. FIG. 7 is a cross-sectional view of a section of the microneedle array of FIG. 6 after the microneedles have been deployed and penetrated the patient's skin. The figure shows skin tissue 50 with an outer surface 52. Beneath the outer surface 52 lie the epidermis 54, dermis 56, and the subcutis or hypodermis 58 layers. The first outwardly facing major surface 22 of film 20 is in contact with outer surface 52 of skin tissue 50.

Microneedles 30*h*, 30*i*, 30*j*, and 30*k* all penetrate outer surface 52 and epidermis 54. Microneedles 30*h*, 30*i* and 30*j* penetrate deeper into dermis 56 than microneedle 30*k*. Also, since proximal end 32*h* of microneedle 30*h* is of a different composition than distal end 34*h* of microneedle 30*h*, the distal end composition is deposited deeper into the dermis than the proximal. The same is true for microneedles 30*j* and 30*k*. So, if there is a desire for personalized treatment at different skin depths, microneedle arrays 10 of the present invention allow a degree of flexibility not available to microneedle arrays produced using the microcasting process.

Also, as discussed earlier, distal end 34*j* of microneedle 30*j* is designed to curve to form a hook-like deployed form upon insertion into the skin. Hook-like microneedle 30*j* may have sufficient strength so as to hold microneedle array 10 intact on the skin during use. This may allow first outwardly facing major surface 22 of film 20 to be free of adhesive.

Figure 8:
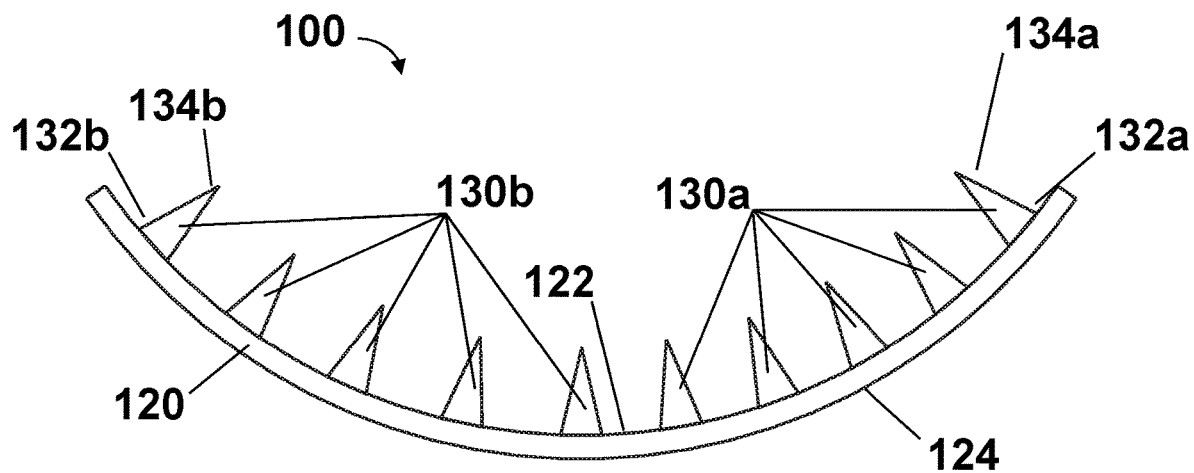
FIG. 8 is a cross-sectional view of a section of a fifth embodiment microneedle array.

In the embodiments shown so far, microneedle array 10 is shown to be planar. In some embodiments, the array may be curvilinear. FIG. 8 is a cross-sectional view of a section of a fifth embodiment microneedle array of the present invention. Microneedle array 100 includes a curved film 120 having first outwardly facing major surface 122 and second outwardly facing major surface 124. First outwardly facing major surface 122 has a plurality of stratum corneum piercing microneedles 130 extending therefrom. The figure shows a plurality of first stratum corneum piercing microneedles 130*a* and a plurality of second stratum corneum piercing microneedles 130*a*. Each microneedle 130*a* has a proximal end 132*a* and a distal end 134*a*, while each microneedle 130*b* has a proximal end 132*b* and a distal end 134*b*. Plurality of first microneedles 130*a* comprises a first benefit agent and plurality of second microneedles 130*b* comprises a second benefit agent. Proximal ends 132*a*, 132*b* are the end of microneedle 130*a*, 130*b* disposed on first outwardly facing major surface 122 of a microneedle array 100.

Figure 9:
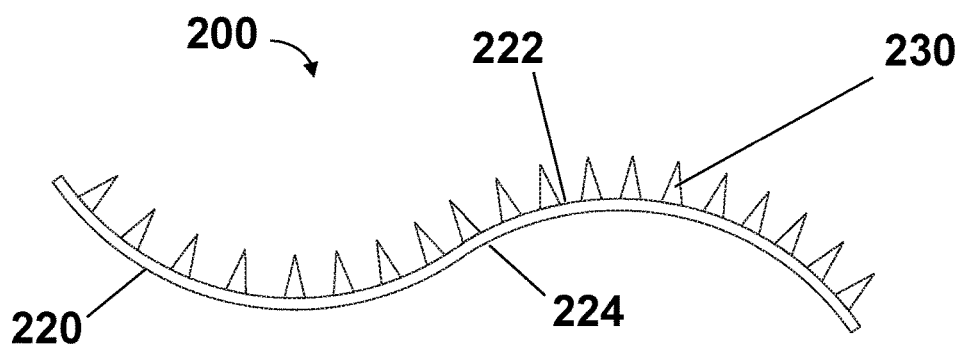
FIG. 9 is a cross-sectional view of a section of a sixth embodiment microneedle array.

FIG. 8 shows microneedle array 100 having a concave shape with respect to microneedles 130. FIG. 9 is a cross-sectional view of a section of a sixth embodiment microneedle array of the present invention. In this embodiment, microneedle array 200 has concave and convex curvature within the array. Microneedle array 200 includes a curved film 220 having first outwardly facing major surface 222 and second outwardly facing major surface 224. First outwardly facing major surface 222 has a plurality of stratum corneum piercing microneedles 230 extending therefrom. As with all other embodiments, microneedle array 200 comprise at least a first benefit agent and a second benefit agent.

Although FIGS. 8 and 9 show curvilinear microneedle arrays in one direction, the array may have multiple axes of curvature in localized regions or overall. Other embodiments may employ multiple axes of curvature to shape the microneedle array.

The curvilinear microneedle arrays shaped to the body surface provides the microneedles oriented normal to that surface. This provides better penetration of the microneedles and retention of the array for treatment.

In preferred embodiments, film 20, 120, 220, stratum corneum piercing microneedles 30, 130, 230, or both, are formed of, or coated with, a biocompatible material. Microneedles 30, 130, 230 may be formed from the same material used in film 20, 120, 220, or alternatively, the microneedles can include a material different from the film material. Representative examples of suitable materials of construction include metals and alloys such as stainless steels, palladium, titanium, and aluminum; plastics such as polyetherimide, polycarbonate, polyetheretherketone, polyimide, polymethylpentene, polyvinylidene fluoride, polyphenylsulfone, liquid crystalline polymer, polyethylene terephthalate (PET), polyethylene terephthalate-glycol modified (PETG), and polyimide; and ceramics such as silicon and glass. The material preferably is selected such that the microneedle is strong enough at its designed dimensions for the microneedle to effectively pierce the skin without significant bending or breaking of the microneedle. The microneedle and substrate materials also should be non-reactive with the drug formulation being delivered by the microneedle array.

In some embodiments, film 20, 120, 220, microneedles 30, 130, 230, or both, are formed of biodegradable or bioabsorbable materials. Representative examples of suitable materials include, but are not limited to, poly(lactic acid) (PLA), poly(glycolic acid) (PGA), polydioxanone (PDO), poly(epsilon-caprolactone) (PCL), poly(lactic-co-glycolic acid) (PLGA), poly(ortho ester) (POE), copoly (ether-ester) (CEE), carboxymethylcellulose (CMC) based formulations, or combinations of such materials.

Film 20, 120, 220, stratum corneum piercing microneedles 30, 130, 230, or both, optionally may further include secondary materials of construction embedded therein or coated thereon. For example, microparticles, nanoparticles, fibers, fibrids, or other particulate materials may be included. These secondary materials may enhance one or more physical or chemical characteristics of microneedle array 10, 100, 200.

In some embodiments, stratum corneum piercing microneedles 30, 130, 230 are formed of biodegradable materials, while film 20, 120, 220 is not biodegradable. In these embodiments the benefit agent material can comprise dissoluble materials or insoluble but dispersible materials. So, the mechanism of delivery of the benefit agent can be, for example, the simultaneous biodegradation of the microneedles with the dissolution or dispersing of the benefit agent. The rate of degradation of the microneedles could be controlled to allow predetermined drug-delivery rates of the benefit agent. In some embodiments, the release rate of first benefit agent could differ from that of second benefit agent. At the point in time when all of the stratum corneum piercing microneedles have degraded, film 20, 120, 220 can be removed from the site of treatment.

In another embodiment, a number of hook-like microneedles 30j may have sufficient strength so as to hold microneedle array 10 intact on the skin during use. This may allow first outwardly facing major surface 22 of film 20 to be free of adhesive. In this embodiment, proximal end 32j of microneedle 30j is of a different composition than distal end 34j of microneedle 30j. If distal end 34j composition is biodegradable, microneedle array 10 may be kept intact on the skin until distal end 34j of hook-like microneedles 30j have degraded. At this point in time, microneedle array 10 may be easily removed from the patient's skin.

In some embodiments, the microneedle array 10 may be further coated with a benefit agent, either the microneedles alone or in combination with the substrate.

Alternatively, the microneedles may have a desired surface structure, such as slight directional ridges, to hold the microneedles in place. The benefit agents may include lubricants, slip agents and the like. Alternatively, the benefit agents may provide one or more benefits to the targeted topical region. Such benefit agents may be any of a variety of compositions, including, without limitation, waxes, oils, emollients, moisturizers, and the like.

Benefit agents may include hyaluronic acid; hydroxyl acids (e.g., glycolic acid, lactic acid, malic acid, salicylic acid, citric acid, tartaric acid); anti-acne agents (e.g., salicylic acid, retinol, retinoids, or other keratolytics, and benzoyl peroxide, or other antimicrobial agents used to treat acne); shine control agents (e.g., rice protein, cotton powder, elubiol (dichlorophenyl-imidazoltioxolan); a retinoid or its derivative such as tretinoin, isotretinoin, motretinide, adapalene, tazarotene, azelaic acid, and retinol; a 5-alpha-reductase inhibitor of amino acids, e.g., glycine derivatives; hydrolyzed vegetable proteins, including soy protein and wheat protein, etc.; green tea (camellia sinesis) extract, and cinnamon bark extract); moisturizers; anti-microbial agents (e.g., cationic antimicrobials such as benzylkonium chloride, benzethonium chloride, triclocarbon, polyhexamethylene biguanide, cetylpyridium chloride, methyl and benzothonium chloride; salts of chlorhexidine, such as Iodopropynyl butylcarbamate, diazolidinyl urea, chlorhexidene digluconate, chlorhexidene acetate, chlorhexidine isethionate, and chlorhexidene hydrochloride; halogenated phenolic compounds, such as 2,4,4'-trichloro-2-hydroxy diphenyl ether (Triclosan); parachlorometa xylenol (PCMX); short chain alcohols, such as ethanol, propanol, and the like); antibiotics or antiseptics (mupirocin, neomycin sulfate bacitracin, polymyxin B, 1-ofloxacin, tetracyclines (chlortetracycline hydrochloride, oxytetracycline-10hydrochloride and tetracycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs), anti-inflammatory agents (e.g., suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts, nonsteroidal anti-inflammatory agents, feverfew (*Tanacetum parthenium*), goji berry (*Lycium barbarum*), milk thistle extract (*Silybum marianum*), amaranth oil (*Amaranthus cruentus*), pomegranate (*Punica granatum*), yerbe mate (*Ilex paraguariensis* leaf extract), white lily flower extract (*Lilium Candidum*), olive leaf extract (*Olea europaea*) and phloretin (apple extract)); anti-mycotic/antifungal agents (e.g., miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs; an azole, an allylamine, or a mixture thereof); external analgesics (e.g., ibuprofen- or diclofenac; capsaicin, fentanyl, and salts thereof such fentanyl citrate; paracetamol (as acetaminophen); non-steroidal anti-inflammatory drugs (NSAIDs) such as salicylates; opioid drugs such as morphine and oxycodone; ibuprofen- or diclofenac-containing gel); anti-oxidants (e.g., sulfhydryl compounds and their derivatives (e.g., sodium metabisulfite and N-acetyl cysteine), lipoic acid and dihydrolipoic acid, resveratrol, lactoferrin; ascorbic acid, ascorbic acid esters, and ascorbic acid derivatives (e.g., ascorbyl palmitate and ascorbyl polypeptide); butylhydroxy anisole, butylated hydroxytoluene (butylhydroxy toluene), retinoids (e.g., retinol and retinyl palmitate), tocopherols (e.g., tocopherol acetate), tocotrienols, and ubiquinone; cysteine, N-acetylcysteine, sodium bisulfite, sodium metabisulfite, sodium formaldehydesulfoxylate, acetone sodium bisulfite, tocopherols, and nordihydroguaiaretic acid; extracts containing flavonoids and isoflavonoids and their derivatives (e.g., genistein and diadzein); extracts containing resveratrol and the like; grape seed, green tea, pine bark, and propolis; plant-derived polyphenol antioxidants such as clove, cinnamon, oregano, turmeric, cumin, parsley, basil, curry powder, mustard seed, ginger, pepper, chili powder, paprika, garlic, coriander, onion and cardamom; typical herbs such as sage, thyme, marjoram, tarragon, peppermint, oregano, savory, basil and dill weed)); depilatory agents (e.g., calcium thioglycolate or potassium thioglycolate); vitamins (e.g., Vitamin A, Vitamin B, Vitamins C, Vitamin E; either alpha, beta, gamma or delta tocopherols, niacin or niacinamide) and vitamin salts or derivatives such as ascorbic acid diglucoside and vitamin E acetate or palmitate; sunblock (e.g., titanium dioxide) and/or sunscreen (e.g., inorganic sunscreens such as titanium dioxide and zinc oxide; organic sunscreens such as octyl-methoxy cinnamates, octyl salicylate, homosalate, avobenzone); vasodilators (e.g., niacin); humectants (e.g., glycerin); anti-aging agents (e.g., retinoids; dimethylaminoathanol (DMAE), copper containing peptides); alpha hydroxy acids or fruit acids and their precursors such as glycolic acid, citric acid, lactic acid, malic acid, mandelic acid, ascorbic acid, alpha-hydroxybutyric acid, alpha-hydroxyisobutyric acid, alphahydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower, and salts and prodrugs thereof); carotenoids, ceramides, fatty acids, enzymes, enzyme inhibitors, minerals, steroids, peptides, amino acids, botanical extracts, colorants, etc. The substances may affect the skin in any of a variety of manners, such as by moisturizing; enhancing skin tone or color (such as with pigments); treating or at least mitigating various skin conditions (such as dry or severe dry skin, eczema, psoriasis, atopic dermatitis, allergic rashes, acne, blackheads, pustules, comedones, rosacea, shingles, wrinkles, cold sores, herpes, corns, warts, sunburn, insect bites, poison ivy, etc.); applying a mechanical force (such as shrinkage) to smooth wrinkles; or, more generally, treating or mitigating the symptoms and appearance of undesired skin imperfections (such as under eye dark circle, redness of acne, fine lines and wrinkles, post inflammatory hyperpigmentation (PIH), redness, inflammation, cellulite, wrinkles, age spots, mottled pigmentation, dark spots, liver spots, under eye puffiness); removing unwanted facial or body hair; aiding in wound healing; etc. For instance, lotions, creams, oils, and even masks may be applied to skin to treat or otherwise to affect the skin. Such personal or consumer healthcare substances are absorbed into the skin generally following the principles of diffusion, under which the rate of diffusion or transport across the skin is correlated with the difference in active concentration on both sides of the skin.

As mentioned earlier, the micromachining or microcasting process for producing microneedle arrays are limited to producing arrays of a single composition. In the present invention, the personalized treatment uses stratum corneum piercing stratum corneum piercing microneedles with more than one benefit agent. So, the micromachining or microcasting process cannot be used.

The microneedle arrays of the present invention can be produced using Additive Manufacturing technology. Additive Manufacturing is a group of techniques used to quickly fabricate a physical part or assembly using three-dimensional computer aided design (CAD) data. Construction of the part or assembly is usually done using "additive layer manufacturing" technologies such as 3D printing. Additive manufacturing is a simple, effective, and economically method of making microneedle arrays which simultaneously delivering more than one benefit agent.

In general, the computer-aided-design-computer-aided manufacturing CAD-CAM workflow is the traditional additive manufacturing process. The process starts with the creation of geometric data, either as a 3D solid using a CAD workstation, or 2D slices using a scanning device. For Additive Manufacturing, this data must represent a valid geometric model; namely, one whose boundary surfaces enclose a finite volume, contains no holes exposing the interior unless they are designed into the structure, and do not fold back on themselves. In other words, the object must have an "inside." The model is valid if for each point in 3D space the algorithm can determine uniquely whether that point lies inside, on, or outside the boundary surface of the model. CAD post-processors will approximate the internal CAD geometric forms with a simplified mathematical form, which in turn is expressed in a specified data format which is a common feature in Additive Manufacturing. To obtain the necessary motion control trajectories to drive the Additive Manufacturing mechanism, the prepared geometric model is typically sliced into layers, and the slices are scanned into lines (producing a "2D drawing" used to generate trajectory as in computer numerical control toolpath), resulting in a layer-to-layer physical building process.

The 3D printing process enables the creation of different sizes and shapes microneedles, as well as the ability to produce microneedle arrays with more than one benefit agent. The location, sharpness, cavitation, and material within individual microneedles can be much more easily controlled with 3D printing than micromachining or microcasting. Soft materials, hard materials, and even liquids can be incorporated into individual microneedles. A change in delivery profile can be designed into the system to make a smart microneedle array. Incompatible compounds may also be built into different sections of the microneedle array without cross contamination fears.

The microneedles need to deliver active/drug at least 100 microns or deeper, but can be designed to have a variable penetration at or above 20 microns. Different applications and uses would need differing levels of penetration, solubility and design features (size, shape, angle, solubility, etc.). In some cases, the benefit agent may be dissolved into the microneedle material, whereas in others it may be stored in a reservoir and delivered through a microfluidic channel in the microneedle.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A microneedle array comprising a film having first and second, outwardly facing major surfaces, wherein the first, outwardly facing major surface has a plurality of stratum corneum piercing microneedles extending therefrom, and wherein the plurality of microneedles includes a plurality of first biodegradable microneedles having a first composition and a first benefit agent dissolved throughout the microneedle material and a plurality of second biodegradable microneedles having a second composition and a second benefit agent dissolved throughout the microneedle material wherein the composition of the plurality of second biodegradable microneedles and the second benefit agent are different from the composition of the plurality of first biodegradable microneedles and the first benefit agent and whereby a rate of biodegradation of the plurality of first and second biodegradable microneedles controls a delivery of the first and second benefit agents.

2. The microneedle array of claim 1 further comprising an adhesive disposed on the first, outwardly facing major surface.

3. The microneedle array of claim 1 wherein the plurality of microneedles each have a height extending from the first, outwardly facing major surface of about 1 micrometer to about 5000 micrometers.

4. The microneedle array of claim 3 wherein the plurality of microneedles all have a substantially uniform height.

5. The microneedle array of claim 3 wherein the plurality of microneedles has variable heights.

6. The microneedle array of claim 1 wherein individual microneedles of the plurality of microneedles are tapered from the first, outwardly facing major surface to a point distal therefrom.

7. The microneedle array of claim 1 wherein individual microneedles of the plurality of microneedles comprise at least one benefit agent.

8. The microneedle array of claim 7 wherein individual microneedles of the plurality of microneedles comprise at least two distinct benefit agents.

* * * * *